(12) United States Patent
Brassart et al.

(10) Patent No.: US 6,489,310 B1
(45) Date of Patent: Dec. 3, 2002

(54) FIBER BLEND FOR ENTERAL COMPOSITION

(75) Inventors: Dominique Brassart, Saint Berthevin (FR); Veronique Jaussan, Morges (CH); Thomas Schweizer, Le Mont-sur-Lausanne (CH); Thierry Brun, Saint Samson (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/857,996

(22) PCT Filed: Dec. 15, 1999

(86) PCT No.: PCT/EP99/10076

§ 371 (c)(1),
(2), (4) Date: Sep. 14, 2001

(87) PCT Pub. No.: WO00/35303

PCT Pub. Date: Jun. 22, 2000

(30) Foreign Application Priority Data

Dec. 15, 1998 (EP) ............................................. 982042459

(51) Int. Cl.$^7$ ...................... A61K 31/715; A61K 35/78; C07H 1/00
(52) U.S. Cl. ........................... 514/54; 514/23; 536/1.11; 536/4.1; 424/757; 426/656; 426/658
(58) Field of Search ................................. 536/1.11, 4.1, 536/123.1; 514/25, 54; 424/757; 426/656, 658

(56) References Cited

PUBLICATIONS

T.F. Schweizer et al., "The physiological and nutritional importance of dietary fibre," Experientia 47, 1991, pp. 181–186.

Quemener, Q. et al., "Determination of Inulin and Oligofructose in Food Products, and Integration in the AOAC Method for Measurement of Total Dietary Fiber," Lebensm–Wiss. U. Technol. vol. 27, 1994, pp. 125–132.

Scheppach, W., et al., "Addition of Dietary Fiber to Liquid Formula Diets: The Pros and Cons," J. of Parenteral and Enteral Nutrition, vol. 14, No. 2, pp. 204–209.

Palacio, J. et al., "Dietary Fiber: A Brief Review and Potential Application to Enteral Nutrition," Nutrition in Clinical Practice, vol. 5, Jun. 1990, pp. 99–106.

Prosky, L. et al., "Determination of Insoluble, Soluble, and Total Dietary Fiber in Foods and Food Products: INterlaboratory Study," J. Assoc. Off. Anal. Chem., vol. 71, No. 5, 1988, pp. 1017–1023.

*Primary Examiner*—Samuel Barts
*Assistant Examiner*—Michael C. Henry
(74) *Attorney, Agent, or Firm*—Bell, Boyd & Lloyd LLC

(57) ABSTRACT

An enteral composition which contains a protein source, a lipid source, a carbohydrate source, and a fibre blend. The fibre blend contains inulin and fructo-oligosaccharides and has 45 to 55% by weight of the blend of soluble fibre and 45 to 55% by weight of the blend of insoluble fibre. The fibre blend may also contain pea inner fibres and pea outer envelope fibres.

10 Claims, No Drawings

FIBER BLEND FOR ENTERAL COMPOSITION

This Application is the National Phase Application of PCT/EP99/10076 filed Dec. 15, 1999.

This invention relates to a fibre blend for enteral compositions. The invention also relates to enteral compositions which contain the fibre blend.

It is now well accepted that dietary fibres should form part of daily food intake. For example, Pilch S. M. (1987; *MD Federation of American Societies for Experimental Biol.*, 223, 84, 2059) recommends that the quantity of dietary fibres in daily food intake of healthy people should be of the order of 27 to 40 g.

Dietary fibres can be classified in according to their properties, their chemical and physical structures, their digestibility during the gastrointestinal transit, or to their physiological properties during the gastrointestinal transit.

Chemically, dietary fibres are considered to comprise polysaccharides or lignin. These compounds are not hydrolysed by endogenous secretions during the gastrointestinal transit (T. Schweizer et al.; 1991; *Experimentia*, 44, p 182–186). The constituent polysaccharides of the dietary fibres may be plant membrane polysaccharides, in particular cellulose, hemicellulose or pectin, or other intracellular polysaccharides which are not hydrolysed by the digestive enzymes, such as resistant starch, galactomannans or inulin (Quemener et al., 1994, *Lebensm. Wiss. u. Technol.*, 27, p 125–132).

Ordinarily, dietary fibres are classified into two categories depending on their biological and physicochemical properties. These categories are insoluble fibres and soluble fibres.

Insoluble fibres, such as cellulose, maize fibres or insoluble soy fibres, have essentially a mechanical role in the gastrointestinal tract. They are generally only very slightly fermented by the intestinal flora and contribute to reducing the duration of the intestinal transit (Scheppach et al., 1990, *JPEN*, 14, p 202–209).

Soluble fibres, such as pectin, inulin or resistant starch, are a very good fermentation substrate for the intestinal flora. The result of this fermentation is a release of fatty acids, in particular short-chain fatty acids in the colon. This has the effect of reducing the pH value in the colon. The result is a reduction in the growth and development of pathogenic bacteria in the colon.

In general, most humans in industrialised societies do not consume enough dietary fibre. However, in a clinical setting, the problem becomes acute. For example, the administration of an enteral composition free of dietary fibres often causes intestinal disorders such as diarrhea or constipation in patients (Palacio et al., 1990; *Nutrition in clinical practice*, 5, p 99–106,). Therefore it has been proposed to include dietary fibres in enteral compositions for clinical nutrition. For example, European patent application 0591267 describes a fibre system for enteral compositions comprising, by weight, 5–50% of gum arabic, 5–25% of sodium carboxymethylcellulose and 45–80% of oat envelope fibres. Further, European patent application 0756828 describes an enteral compositions which contains dietary fibres for maintaining good intestine function. This composition, which is in liquid form or in dried form, contains, per 2000 kcal, 15–50% of soluble dietary fibres, 15–45% of insoluble dietary fibres and 8–70% of oligosaccharides or of resistant starch.

However, most known enteral compositions do not contain a balance of soluble and insoluble dietary fibres. Further, those compositions which contain higher proportions of soluble fibres are often too viscous for tube feeding. Problems with stability also arise.

Accordingly this invention provides a fibre blend for an enteral composition, the fibre blend comprising pea inner fibres, pea outer envelope fibres, inulin, and fructo-oligosaccharides.

The fibre blend provides the enteral composition with good mechanical properties and good nutritional and biological properties. The mechanical properties include decreasing in the duration of gastrointestinal transit. The nutritional and biological properties include the release of short-chain fatty acids for maintaining bacterial balance in intestinal mucosa and to avoiding the growth and development of pathogenic bacteria. The fibre blend may act on the entire gastrointestinal system, at the level of the stomach, the small intestine and the colon. Further, a balance between soluble and insoluble fibres may be obtained without the enteral composition becoming too viscous.

The fibre blend may contain about 20 to about 50% by weight of pea inner fibres, about 20 to about 50% by weight of pea outer envelope fibres, about 5% to about 30% by weight of inulin, and about 10% to about 40% by weight of fructo-oligosaccharides.

The invention also provides an enteral composition which contains the fibre blend defined above. The enteral composition may also contain a protein source, a carbohydrate source, and a lipid source.

Preferably, the protein source provides about 10% to about 20% of energy, the lipid source provides about 30% to about 50% of energy, and the carbohydrate source provides about 35% to about 55% of energy.

In another aspect, this invention provides an enteral composition which comprises a protein source, a lipid source, a carbohydrate source, and a fibre blend comprising inulin and fructo-oligosaccharides and having 45 to 55% by weight of the blend of soluble fibre and 45 to 55% by weight of the blend of insoluble fibre.

In further aspect, this invention provides an enteral composition which comprises a protein source, a lipid source, a carbohydrate source, and a fibre blend comprising about 20% to about 40% by weight of inulin and about 60% to about 80% by weight of fructo-oligosaccharides.

The enteral composition may be in liquid form or in the form of a soluble powder which is reconstituteable in an aqueous liquid to provide a liquid nutritional composition. The enteral composition may also be in other enterally administrable forms such as desserts, cereals, snack bars, and the like.

Embodiments of the invention are now described, by way of example only.

In this specification, the term "soluble fibre" means those dietary fibres which are characterised as soluble using the method of Prosky et al; 1988; *J. Assoc. Off. Anal. Chem*, 70, 5, 1017. This is the official method of the Association of Official Analytical Chemists. The term "insoluble fibre" means those dietary fibres which are characterised as insoluble using the method of Prosky et al.

The invention provides a fibre blend which contains inulin and fructo-oligosaccharides. This blend has optimum bifidogenic effect and production of short chain fatty acids in the colon. The fibre blend may have roughly equivalent amounts of soluble fibre and insoluble fibre. The fibre blend may also contain pea inner fibres and pea outer envelope fibres.

Within the context of this specification the term "pea inner fibres" is taken to mean fibres from inside the pea outer envelope or testa. They comprise cellulose, hemicellulose and pectin; for example about 15% by weight of cellulose, about 45% by weight of hemicellulose and about 40% by weight of pectin. With this fibre distribution, about 66% by weight of the fibres are insoluble fibres. Therefore pea inner fibres contribute mechanically to gastrointestinal transit by reducing the transit time. Further, components of pea inner fibre are fermented by intestinal flora to release short-chain fatty acids. This release causes a reduction in pH in the colon and, as a result, a decrease in the growth and development of the pathogenic bacteria in the colon. Suitable pea inner fibres are commercially available.

The release of fatty acids is of great importance for patients being treated with antibiotics because, during antibiotic treatment, the integrity and function of the intestinal flora is compromised. A diet high in soluble fibres reduces these effects. Moreover, the release of short-chain fatty acids, such as butyrate, causes the absorption of water coupled with absorption of sodium ions in the colon. This has the effect of diarrhea. Also, butyrate is a high-energy substrate for the colonocytes.

Within the context of this specification the term "pea outer envelope fibres" is taken to mean fibres from the pea outer envelope or testa. They comprise cellulose, hemicellulose and lignin; for example about 68% by weight of cellulose, about 25% by weight of hemicellulose and about 7% by weight of lignin. With this fibre distribution, about 10% by weight of the fibres are insoluble fibres and about 90% by weight are insoluble fibres. Therefore pea a touter envelope fibres contribute mechanically to gastrointestinal transit by reducing the transit time and have a positive effect on the capacity to retain water in the intestine. Suitable pea outer envelope fibres are commercially available.

Inulin is a soluble fibre which is present in numerous plants, such as asparagus, artichokes, onions, wheat or chicory, for example. Inulin is not digested in the small intestine; instead it is fermented in the colon. The main effects of inulin fibres on the digestive system are a decrease in the duration of the intestinal transit, a decrease in the level of glycemia, a decrease in the lipid content in the blood, a decrease in the pH in the colon, decrease constipation and a bifidogenic effect. Thus, inulin can be fermented by bifidobacteria, which has the consequence of increasing the concentration of these bacteria at the level of the intestinal flora and of decreasing the concentration of enterobacteria, in particular Clostridiae, at the level of the intestinal flora.

The inulin may be provided in the form of a natural extract which is suitable for human consumption. Extracts from chicory are particularly suitable.

The extract preferably contains at least 80% by weight of inulin; more preferably at least 90% by weight of inulin. The inulin preferably has a degree of polymerisation of at least about 8; for example about 10 to about 25. Suitable inulin extracts may be obtained from Orafti SA of Tirlemont 3300, Belgium under the trade mark "Raftiline". For example, the inulin may be provided in the form of Raftiline® DST which is a fine white powder which contains about 90 to about 94% by weight of inulin, up to about 4% by weight of glucose and fructose, and about 4 to 9% by weight of sucrose. The average degree of polymerisation of the inulin is about 10 to about 12.

The fructo-oligosaccharides are soluble fibres which are in the form of fructose oligomers containing 1-kestose (GF2), nystose(GF3), and 1F-fructofuranosyl nystose(GF4), in which fructosyl units(F) are bound at the β-2,1 position of sucrose(GF) respectively. Generally amounts of sucrose, and glucose may also be present. The fructo-oligosaccharides may be obtained by hydrolysing inulin, by enzymatic methods, or by using micro-organisms. The fructo-oligosaccharides may be obtained commercially, for example from Orafti SA of Tirlemont 3300, Belgium under the trade mark "Raftilose", or from Meiji Seika Co. of Japan. For example, the inulin may be provided in the form of Raftilose®P95.

The inulin and the fructo-oligosaccharides are reported to promote the growth of bifidobacteria in the gastro-intestinal tract and, in certain circumstances prevent or decrease the growth of pathogens such as Clostridiae. Further, promoting the growth of bifidobacteria is reported to have various other beneficial effects. Moreover, inulin and the fructo-oligosaccharides may reduce blood glucose levels.

The blend has the particular advantage of providing optimum bifidogenic effect and production of short chain fatty acids in the colon. It is found that fructo-oligosaccharides have a greater bifidogenic effect than inulin but that inulin has delayed fermentation such that it is preferentially fermented in the colon. By selecting a mixture of inulin and fructo-oligosaccharides, both the bifidogenic effect and production of short chain fatty acids in the colon may be maximised.

The fibre blend may also contain other oligosaccharides if desired. Suitable examples are galacto-oligosaccharides, xylo-oligosaccharides or oligo derivatives of starch.

The amounts of the components of the fibre blend are preferably selected such that the fibre blend comprises about 45 to about 55% by weight of soluble fibres and about 45% to about 55% by weight of insoluble fibres. This proportion makes it possible to best exploit the advantages of each of these two fibre types. Preferably the weight ratio of soluble fibres to insoluble fibres is about 1:1.

Further, the amounts of the components of the fibre blend are preferably selected such that the fibre blend comprises about 20% to about 40% by weight of inulin and about 60% to about 80% by weight of fructo-oligosaccharides. For example, the fibre blend may comprise about 30% by weight of inulin and about 70% by weight of fructo-oligosaccharides.

Preferably the fibre blend comprises about 20 to about 50% by weight of pea inner fibres, about 20 to about 50% by weight of pea outer envelope fibres, about 5% to about 30% by weight of inulin, and about 10% to about 40% by weight of fructo-oligosaccharides. For example, the fibre blend may comprise about 30 to about 40% by weight of pea inner fibres, about 30 to about 40% by weight of pea outer envelope fibres, about 5% to about 15 by weight of inulin, and about 20% to about 30% by weight of fructo-oligosaccharides.

The fibre blend may be included in an enteral composition. The enteral composition may comprise about 1% to about 5% by weight of the fibre blend; for example about 1% to about 2% by weight.

Preferably, the enteral composition includes a protein source, a carbohydrate source and a lipid source.

The protein source is preferably a high quality protein source; for example milk protein, whey protein, casein protein, or soy protein, or mixtures of these proteins. The protein source may be in the form of intact protein or may be hydrolysed. Other protein sources such as rice, pea and oat protein, or mixtures thereof, may also be used. Further, if desired, the protein source may include free amino acids.

The protein source preferably provides about 10% to about 25% of the energy of the composition. For example, the protein source may provide about 12% to about 18% of the energy of the composition; preferably about 15% of the energy of the composition.

Preferably, the carbohydrate source may be any suitable carbohydrate or carbohydrate mixtures. For example, the carbohydrate source may be maltodextrin, modified starch, amylose starch, tapioca starch, corn starch, or fructose, or mixtures thereof. Maltodextrin is preferred if low osmolarity is required.

The carbohydrate source provides about 35% to about 60% of the energy of the composition; preferably about 45% to about 55% of the energy. For example, the carbohydrate source may provide about 50% of the energy of the composition.

The lipid source preferably contains monounsaturated fatty acids;

polyunsaturated fatty acids (omega-3 and omega-6 fatty acids), and/or saturated fatty acids. Preferably the polyunsaturated fatty acids provide up to about 30% of the weight of the lipid source. For example the polyunsaturated fatty acids may provide about 15% to about 25% of the weight of the lipid source. The lipid profile of the enteral composition is preferably designed to have a polyunsaturated fatty acid omega-6 (n-6) to omega-3 (n-3) ratio of about 4:1 to about 10:1. Saturated fatty acids preferably provide about 30% to about 70% of the weight of the lipid source; for example about 50% to about 65% by weight. The majority of the saturated fatty acids are preferably in the form of medium chain triglycerides. For example, medium chain triglycerides may make up about 20% to about 70% by weight of the lipid source.

Suitable sources of lipids are olive oil, corn oil, sunflower oil, rapeseed oil, corn oil, hazelnut oil, safflower oil, and the like. Fractionated coconut oils are a suitable source of medium chain triglycerides. A mixture of corn oil, rapeseed oil, medium chain triglycerides and soy oil may be used.

The lipid source may provide about 25% to about 45% of the energy of the composition; preferably about 30% to about 45%. For example, the lipid source may provide about 35% of the energy of the composition.

For clinical applications, the enteral composition preferably includes a complete vitamin and mineral profile. For example, sufficient vitamins and minerals may be provided to supply about 25% to about 250% of the recommended daily allowance of the vitamins and minerals per 1000 calories of the nutritional composition.

For clinical applications, the enteral composition conveniently has an osmolarity of about 200 mOsm/l to about 400 mOsm/l; for example about 250 mOsm/l to about 350 mOsm/l.

For clinical applications, the energy density of the enteral composition is preferably about 700 kcal/l to about 1500 kcal/l; for example about 1000 kcal/l.

For clinical applications, the enteral composition is preferably in the form of a ready-to-use formulation. In this form, the composition may be fed to a patient via a nasogastric tube, jejunum tube or by having the patient drink it. As such, the enteral composition may be in a variety of forms; for example as a fruit juice-type beverage, a milk shake-type beverage and the like. However, the enteral composition may also be in soluble powder form to be reconstituted prior to use.

Various flavours, sweeteners and other additives may be present. Artificial sweeteners such as acetosulfame and L-aspartyl based sweeteners may be used; for example aspartame.

The enteral composition may be produced as is conventional; for example, by blending together the protein source, the carbohydrate source, and the lipid source. If used, the emulsifiers may be included in the blend. The vitamins and minerals may be added at this point but are usually added later to avoid thermal degradation. Any lipophilic vitamins, emulsifiers and the like may be dissolved into the lipid source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture is then homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point.

For a product in liquid form, the homogenised mixture is preferably aseptically filled into suitable containers. Aseptic filling of the containers may be carried out by pre-heating the homogenised mixture (for example to about 75 to 85° C.) and then injecting steam into the homogenised mixture to raise the temperature to about 140 to 160° C.; for example at about 150° C. The homogenised mixture may then be cooled, for example by flash cooling, to a temperature of about 75 to 85° C. The homogenised mixture may then be further homogenised, cooled to about room temperature and filled into containers. Suitable apparatus for carrying out aseptic filling of this nature is commercially available.

For a product in powder form, the homogenised mixture is dried to powder; for example by spray drying. Conventional procedures may be used.

When in a liquid form suitable for use in clinical nutrition, the enteral composition may be easily administered by tube feeding, either by gravity, or using a pump. In this form, the enteral composition may have a viscosity of less than about 12 cp at room temperature.

The enteral composition may be used as a nutritional support for human and animal patients; particularly patients requiring long term nutritional support. Further, the enteral composition is suitable for patients with normal digestive function.

It will be appreciated that the enteral composition may be in forms other than those suitable for clinical nutrition. For example, the enteral composition may be in the form of desserts, cereals, yoghurts, snack bars, and the like. If fed to pets, the enteral composition may be in the form of dried kibbles, meat emulsions, and formulated emulsion products.

Specific examples of the fibre blend are now described for further illustration.

EXAMPLE 1

An enteral composition is prepared by mixing together pea inner fibres, pea outer envelope fibres, fructo-oligosaccharides and inulin in demineralized water at about 65–70° C. The amounts of each component are selected to provide 4 g/l of pea inner fibres, 4 g/l of pea outer envelope fibres, 2.8 g/l of fructo-oligosaccharides and 1.2 g/l of inulin in the final product. The mixture is stirred for 5 minutes, homogenised, and stored under stirring.

A lipid phase is prepared by mixing corn oil, rapeseed oil, soy oil and medium chain triglycerides in an amount to provide 39 g/l of lipid in the final product. About 1.4 g/l of an emulsifier, glycerol stearate, is added.

The lipid phase is then mixed with the fibre mixture and homogenised. The emulsion obtained is cooled to 60° C. About 38 g/l of a protein mixture comprising casein and soy protein, about 125 g/l of carbohydrate, and mineral are added. An aqueous vitamin solution is then added. The pH is then adjusted to 7.1.

The enteral composition is heat-treated at 150° C. for 6 seconds, cooled, aseptically filled into flexible contains and stored at room temperature.

The components of the enteral composition are as follows:

| Component | Amount (g/l) |
| --- | --- |
| Protein (casein and soy) | 38 |
| Lipid (corn, rapeseed, soy and MCT) | 39 |
| Carbohydrates (maltodextrin) | 125 |
| Fibres | 12 |
| Soluble | 6 |
| Insoluble | 6 |
| Vitamins and minerals | As desired |

The ω-6:ω-3 ratio is 7 and the osmolarity is 270 mosm/l.

After one month's storage, the particle size, the viscosity, the texture and the stability of the enteral composition are determined. Further, a taste evaluation of the enteral composition is carried out. The results are as follows:

| Measurements | |
| --- | --- |
| Particle size | <50 μm |
| Viscosity | 6 cp |
| Texture | creamy |
| Taste evaluation | neutral |
| Stability (measurement of sediment) | good |

The results demonstrate that the enteral composition has characteristics which are highly advantageous for its use in the field of enteral nutrition. For example, this composition, because of its low viscosity, may be readily tube fed using gravity. Moreover, the composition has excellent stability.

EXAMPLE 2

The enteral composition of example 1 is administered to patients by the enteral route, using gravity. The enteral composition flows to the patient at a regular flow rate.

What is claimed is:

1. A fibre blend for an enteral composition, the fibre blend comprising pea inner fibres, pea outer envelope fibres, inulin, and fructo-oligosaccharides.

2. A fibre blend according to claim 1 which comprises 20 to 50% by weight of pea inner fibres, 20 to 50% by weight of pea outer envelope fibres, 5% to 30% by weight of inulin, and 10% to 40% by weight of fructo-oligosaccharides.

3. A fibre blend according to claim 2 which comprises 30 to 40% by weight of pea inner fibres, 30 to 40% by weight of pea outer envelope fibres, 5% to 15% by weight of inulin, and 20% to 30% by weight of fructo-oligosaccharides.

4. A fibre blend according to claim 2 which contains 45 to 55% by weight of soluble fibre and 45 to 55% by weight of insoluble fibre.

5. An enteral composition which comprises a protein source, a lipid source, a carbohydrate source, and a fibre blend comprising pea inner fibres, pea outer envelope fibres, inulin, and fructo-oligosaccharides.

6. An enteral composition according to claim 5 in which the fibre blend comprises 20 to 50% by weight of pea inner fibres, 20 to 50% by weight of pea outer envelope fibres, 5% to 30% by weight of inulin, and 10% to 40% by weight of fructo-oligosaccharides.

7. An enteral composition according to claim 6 in which the fibre blend comprises 30 to 40% by weight of pea inner fibres, 30 to 40% by weight of pea outer envelope fibres, 5% to 15 by weight of inulin, and 20% to 30% by weight of fructo-oligosaccharides.

8. An enteral composition according to claim 6 in which the fibre blend contains 45 to 55% by weight of soluble fibre and 45 to 55% by weight of insoluble fibre.

9. An enteral composition which comprises a protein source, a lipid source, a carbohydrate source, and a fibre blend comprising inulin and fructo-oligosaccharides and having 45 to 55% by weight of the blend of soluble fibre and 45 to 55% by weight of the blend of insoluble fibre.

10. An enteral composition which comprises a protein source, a lipid source, a carbohydrate source, and a fibre blend comprising about 20% to about 40% by weight of inulin and about 60% to about 80% by weight of fructo-oligosaccharides.

* * * * *